US00PP33551P2

(12) United States Plant Patent
Mathey

(10) Patent No.: US PP33,551 P2
(45) Date of Patent: Oct. 12, 2021

(54) ***SORBARIA* PLANT NAMED 'SMNSSC'**

(50) Latin Name: *Sorbaria sorbifolia*
Varietal Denomination: SMNSSC

(71) Applicant: Megan M. Mathey, Holland, MI (US)

(72) Inventor: Megan M. Mathey, Holland, MI (US)

(73) Assignee: SPRING MEADOW NURSERY INC., Grand Haven, MI (US)

( * ) Notice: Subject to any disclaimer, the term of this patent is extended or adjusted under 35 U.S.C. 154(b) by 0 days.

(21) Appl. No.: 17/039,976

(22) Filed: Sep. 30, 2020

(51) Int. Cl.
*A01H 5/12* (2018.01)
*A01H 6/74* (2018.01)

(52) U.S. Cl.
USPC ..... Plt./226
CPC ..... *A01H 6/74* (2018.05); *A01H 5/12* (2013.01)

(58) Field of Classification Search
USPC ..... Plt./226
CPC ..... A01H 6/74
See application file for complete search history.

*Primary Examiner* — Anne Marie Grunberg
(74) *Attorney, Agent, or Firm* — C. Anne Whealy

(57) ABSTRACT

A new and distinct cultivar of *Sorbaria* plant named 'SMNSSC', characterized by its relatively compact, upright, outwardly spreading and uniform plant habit; moderately vigorous growth habit; freely branching habit; leaves that are yellow green and dark reddish orange in color during the spring becoming green in color during the summer; upright and narrow panicles with numerous white-colored flowers; and good garden performance and winter hardiness.

2 Drawing Sheets

Figure 1:
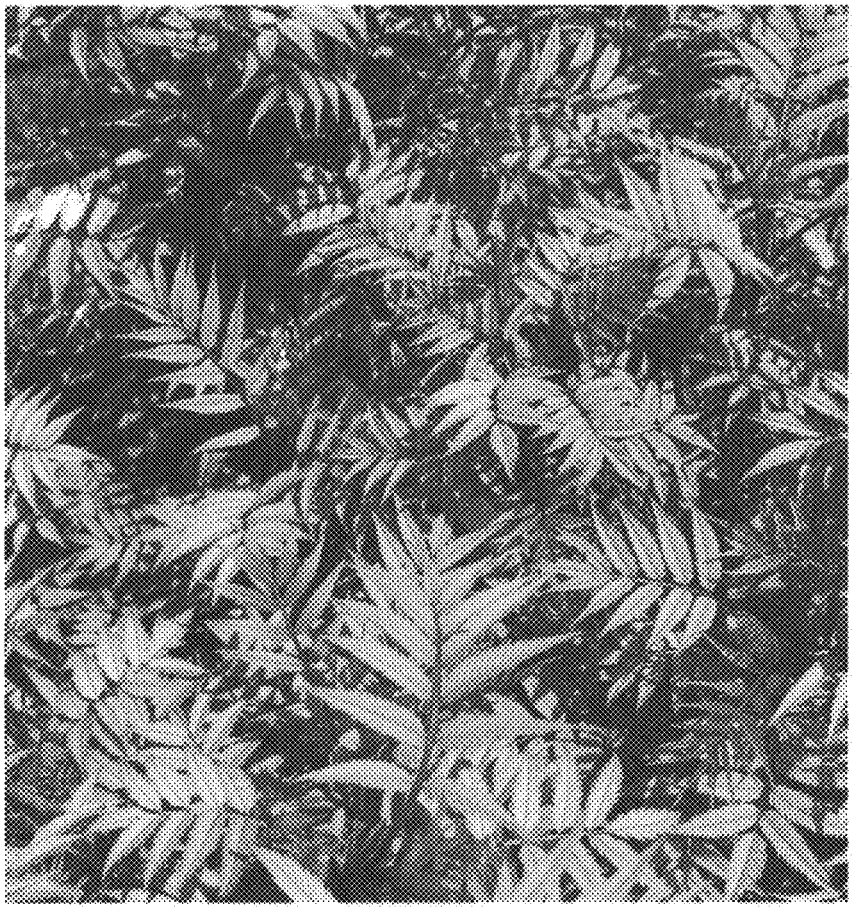

Botanical designation: *Sorbaria sorbifolia.*
Cultivar denomination: 'SMNSSC'.

STATEMENT REGARDING PRIOR DISCLOSURES BY INVENTOR/APPLICANT & ASSIGNEE

The Inventor/Applicant and Assignee assert that no publications nor advertisements relating to sales, offers for sale or public distribution occurred more than one year prior to the effective filing date of this application. Any information about the claimed plant would have been obtained from a direct or indirect disclosure from the Inventor/Applicant and/or the Assignee. Inventor/Applicant and Assignee claim a prior art exemption under 35 U.S.C. 102(b)(1) for disclosure and/or sales prior to the filing date but less than one year prior to the effective filing date.

BACKGROUND OF THE INVENTION

The present invention relates to a new and distinct *Sorbaria* plant, botanically known as *Sorbaria sorbifolia*, commonly referred to as False Spiraea and hereinafter referred to by the name 'SMNSSC'.

The new *Sorbaria* plant is a whole plant mutation of *Sorbaria sorbifolia* 'Sem', disclosed in U.S. Plant Pat. No. 16,336. The new *Sorbaria* plant was discovered and selected by the Inventor during the summer of 2018 as a single plant from within a population of plants of the mutation parent in a controlled environment in Grand Haven, Mich.

Asexual reproduction of the new *Sorbaria* plant by softwood stem cuttings in a controlled environment in Grand Haven, Mich. since the summer of 2018 has shown that the unique features of this new *Sorbaria* plant are stable and reproduced true to type in successive generations of asexual reproduction.

SUMMARY OF THE INVENTION

Plants of the new *Sorbaria* have not been observed under all possible combinations of environmental conditions and cultural practices. The phenotype may vary somewhat with variations in environmental conditions such as temperature and light intensity without, however, any variance in genotype.

The following traits have been repeatedly observed and are determined to be the unique characteristics of 'SMNSSC'. These characteristics in combination distinguish 'SMNSSC' as a new and distinct *Sorbaria* plant:

1. Relatively compact, upright, outwardly spreading and uniform plant habit.
2. Moderately vigorous growth habit.
3. Freely branching habit.
4. In the spring, leaves are yellow green and dark reddish orange in color becoming green in color during the summer.
5. Upright and narrow panicles with numerous white-colored flowers.
6. Good garden performance and winter hardiness.

Plants of the new *Sorbaria* can be compared to plants of the mutation parent, 'Sem'. Plants of the new *Sorbaria* differ from plants of 'Sem' in the following characteristics:

1. Plants of the new *Sorbaria* are more compact than plants of 'Sem'.
2. Plants of the new *Sorbaria* produce none to few suckers whereas plants of 'Sem' readily produce suckers.
3. Leaves of plants of the new *Sorbaria* retain their spring coloration longer than leaves of plants of 'Sem'.

Plants of the new *Sorbaria* can be compared to plants of the *Sorbaria sorbifolia* 'Emerald Charm', not patented. In side-by-side comparisons, plants of the new *Sorbaria* differ from plants of 'Emerald Charm' in the following characteristics:

1. In the spring, leaves of plants of the new *Sorbaria* are yellow green and dark reddish orange in color whereas leaves of plants of 'Emerald Charm' are lime green and yellow to orange in color during the spring.
2. In the summer, leaves of plants of the new *Sorbaria* are darker green in color than leaves of plants of 'Emerald Charm' in the summer.

BRIEF DESCRIPTION OF THE PHOTOGRAPHS

The accompanying colored photographs illustrate the overall appearance of the new *Sorbaria* showing the colors as true as it is reasonably possible to obtain in colored reproductions of this type. Colors in the photographs may differ slightly from the color values cited in the detailed botanical description which accurately describe the colors of the new *Sorbaria*.

The photograph on the first sheet (FIG. 1) is a top perspective view of a typical plant of 'SMNSSC' grown in an outdoor nursery during the spring.

Figure 2:
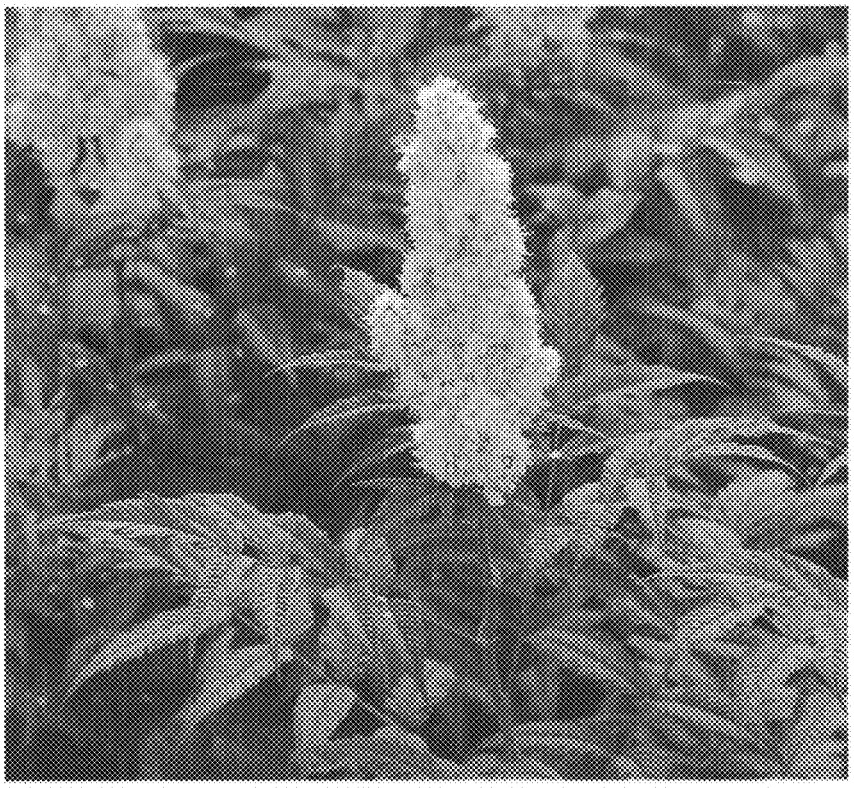

The photograph on the second sheet (FIG. 2) is a close-up view of a flowering plant of 'SMNSSC' grown in an outdoor nursery during the summer.

DETAILED BOTANICAL DESCRIPTION

The aforementioned photographs and following observations, measurements and values describe plants grown during the spring and summer in ground beds in an outdoor nursery and in three-gallon containers in a polyethylene-covered greenhouse in Grand Haven, Mich. and under cultural practices typical of commercial *Sorbaria* production. During the production of the plants, day temperatures ranged from 18° C. to 27 ° C. and night temperatures ranged from ranged from 5° C. to 10° C. Plants were two years old when the photographs and the description were taken. In the description, color references are made to The Royal Horticultural Society Colour Chart, 2015 Edition, except where general terms of ordinary dictionary significance are used.

Botanical classification: *Sorbaria sorbifolia* 'SMNSSC'.

Parentage: Whole plant mutation of *Sorbaria sorbifolia* 'Sem', disclosed in U.S. Plant Pat. No. 16,336.

Propagation:

*Type*.—By softwood stein cuttings.

*Time to initiate roots, summer*.—About 15 days at temperatures about 18° C. to 27° C.

*Time to produce a rooted young plant, summer*.—About six months at temperatures about 18° C. to 27° C.

*Root description*.—Fine; fibrous; typically brownish white in color, actual color of the roots is dependent on substrate composition, water quality, fertilizer, substrate temperature and physiological age of roots.

*Rooting habit*.—Freely branching; dense.

Plant description:

*Plant and growth habit*.—Perennial shrub; relatively compact, upright, outwardly spreading and uniform plant habit; moderately vigorous growth habit and rapid growth rate.

*Plant height*.—About 54 cm.

*Plant diameter* (*area of spread*).—About 80 cm.

Lateral branch description:

*Branching habit*.—Freely branching habit with about seven lateral branches developing per plant; pinching enhances lateral branch development.

*Length*.—About 46 cm.

*Diameter*.—About 4 mm.

*Internode length*.—About 2 cm.

*Texture*.—Smooth, glabrous.

*Aspect*.—Erect to about 45° from vertical.

*Color*.—Close to 144B.

Leaf description:

*Arrangement*.—Alternate; compound with about 11 leaflets per leaf.

*Leaf length*.—About 7 cm.

*Leaf width*.—About 2 cm.

*Shape*.—Lanceolate.

*Apex*.—Acute.

*Base*.—Attenuate.

*Margin*.—Bi-serrate.

*Texture, upper and lower surfaces*.—Rugose, glabrous.

*Venation pattern*.—Pinnate.

*Color*.—Developing leaves, upper and lower surfaces: Close to between 153A to 154B tinged with close to 169D. Fully expanded leaves, upper surface: Close to 146A tinged with close to 178B; color becoming closer to 146A with subsequent development; venation, close to 151A. Fully expanded leaves, lower surface: Close to 147C; venation, close to 145D.

*Petioles*.—Length: About 3 cm to 5 cm. Diameter: About 1.5 mm. Texture, upper and lower surfaces: Smooth, glabrous. Color, upper surface: Close to 152B tinged with close to 180A. Color, lower surface: Close to 144D.

Flower description:

*Flower type and flowering habit*.—Single small rotate flowers arranged on terminal panicles; panicles narrowly conical in shape and are usually upright to arching outwardly; freely flowering habit with more than 100 flowers developing per inflorescence and numerous inflorescences developing per plant during the flowering season; flowers face upright to outwardly depending on the position on the inflorescence; flowers not persistent.

*Fragrance*.—Fragrant, bitter.

*Natural flowering season*.—Plants flower during the summer in Michigan.

*Flower buds*.—Height: About 3 mm. Diameter: About 3 mm. Shape: Ovoid. Color: Close to NN155C.

*Inflorescence length*.—About 10 cm.

*Inflorescence diameter*.—About 4 cm.

*Flower diameter*.—About 1 cm.

*Flower depth*.—About 4 mm.

*Petals*.—Quantity per flower: Typically five in a single whorl. Length: About 4 mm. Width: About 3 mm. Shape: Elliptical. Apex: Acute. Base: Obtuse. Margin: Entire. Texture, upper and lower surfaces: Smooth, glabrous; delicate. Color: Developing petals, upper and lower surfaces: Close to NN155C. Fully developed petals, upper and lower surfaces: Close to NN155C.

*Sepals*.—Quantity and arrangement: Typically five sepals per flower arranged in a single whorl, fused at the base. Length: About 1 mm. Diameter: About 1 mm. Shape: Deltoid. Apex: Acute. Margin: Entire. Texture, upper and lower surfaces: Smooth, glabrous. Color, upper and lower surfaces: Close to 144B.

*Peduncles*.—Length: About 6.5 cm. Diameter: About 1 mm. Strength: Strong, flexible. Angle: Upright to outwardly. Texture: Smooth, glabrous. Color: Close to 144C.

*Pedicels*.—Length: About 6 mm. Diameter: About 1 mm. Strength: Strong, flexible. Angle: About 45° from the peduncle axis. Texture: Smooth, glabrous. Color: Close to 144C.

*Reproductive organs*.—Stamens: Quantity per flower: Typically 20. Filament length: About 4 mm. Filament color: Close to NN155C. Anther length: About 1 mm. Anther shape: Club-shaped. Anther color: Close to NN155C. Pollen amount: Moderate. Pollen color: Close to NN155C. Pistils: Quantity per flower: One. Pistil length: About 4 mm. Style length: About 3 mm. Style color: Close to 145D. Stigma shape: Globular. Stigma color: Close to 145D. Ovary color: Close to 145D.

*Seeds and fruits*.—To date, seed and fruit development have not been observed on plants of the new *Itea*.

Garden performance: Plants of the new *Sorbaria* have been observed to have good garden performance and to tolerate rain, wind and temperatures ranging from about −32° C. to about 36° C.

Pathogen & pest resistance: To date, plants of the new *Sorbaria* have not been shown to be resistant to pathogens and pests common to *Sorbaria* plants.

It is claimed:

1. A new and distinct *Sorbaria* plant named 'SMNSSC' as illustrated and described.

* * * * *